(12) United States Patent
Watson

(10) Patent No.: US 9,180,219 B2
(45) Date of Patent: Nov. 10, 2015

(54) COMPOSITIONS COMPRISING HONEY AND A SUPER-ABSORBENT MATERIAL

(71) Applicant: ManukaMed Limited, Masterton (NZ)

(72) Inventor: Denis Eric Watson, Masterton (NZ)

(73) Assignee: ManukaMed Limited, Materton (NZ)

( * ) Notice: Subject to any disclaimer, the term of this patent is extended or adjusted under 35 U.S.C. 154(b) by 0 days.

(21) Appl. No.: 14/025,407

(22) Filed: Sep. 12, 2013

(65) Prior Publication Data

US 2014/0127283 A1 May 8, 2014

Related U.S. Application Data

(63) Continuation of application No. 12/996,146, filed as application No. PCT/GB2009/001407 on Jun. 5, 2009, now abandoned.

(30) Foreign Application Priority Data

Jun. 6, 2008 (GB) ...................................... 0810404

(51) Int. Cl.

| A61L 15/60 | (2006.01) |
|---|---|
| A61L 15/40 | (2006.01) |
| A61L 15/26 | (2006.01) |
| A61K 9/70 | (2006.01) |
| A61L 15/44 | (2006.01) |

(52) U.S. Cl.
CPC .................. *A61L 15/40* (2013.01); *A61L 15/26* (2013.01); *A61L 15/44* (2013.01); *A61L 15/60* (2013.01); *A61L 2300/30* (2013.01); *A61L 2300/404* (2013.01)

(58) Field of Classification Search
CPC ......... A61L 15/26; A61L 15/40; A61L 15/44; A61L 15/60; A61L 2300/30; A61L 2300/404
See application file for complete search history.

(56) References Cited

U.S. PATENT DOCUMENTS

| 3,812,252 A | 5/1974 | Silvetti |
| 4,401,651 A | 8/1983 | Knutson |
| 4,414,202 A | 11/1983 | Silvetti |
| 4,883,478 A | 11/1989 | Lerailler et al. |
| 4,950,475 A | 8/1990 | Vishnupad et al. |
| 5,177,065 A | 1/1993 | Silvetti, Sr. et al. |
| 5,482,932 A | 1/1996 | Thompson |
| 5,750,175 A | 5/1998 | Hubbell |
| 5,759,570 A | 6/1998 | Arnold |
| 5,879,717 A | 3/1999 | McConn-Stern et al. |
| 5,941,840 A | 8/1999 | Court et al. |
| 5,980,875 A | 11/1999 | Mousa |
| 6,011,194 A | 1/2000 | Buglino et al. |
| 6,123,958 A | 9/2000 | Cheong et al. |
| 6,146,655 A | 11/2000 | Ruben |
| 6,171,604 B1 | 1/2001 | Mousa |
| 6,419,935 B1 | 7/2002 | Gueret |
| RE42,755 E | 9/2011 | Molan |
| 8,303,551 B2 | 11/2012 | Bray et al. |
| 2004/0127826 A1 | 7/2004 | Caskey |
| 2005/0287191 A1 | 12/2005 | Munro et al. |
| 2007/0088106 A1* | 4/2007 | Schlesiger et al. ............... 524/42 |

FOREIGN PATENT DOCUMENTS

| AU | 2007100007 A4 | 2/2007 |
| EP | 0258761 B1 | 3/1988 |
| GB | 2382527 | 6/2003 |
| JP | 2004-527453 | 9/2004 |
| JP | 2005-511146 | 4/2005 |
| JP | 2006-271927 | 10/2006 |
| WO | WO 0141776 A2 * | 6/2001 |
| WO | 2007/068477 A1 | 6/2007 |

OTHER PUBLICATIONS

Bulman, Michael W. et al., "Honey as a Surgical Dressing," Middlesex Hospital Journal, vol. 55:188-189 (1955).

Efem, S.E, "Recent advances in the management of Fournier's gangrene: preliminary observations," Surgery, vol. 113(2):200-204 (1993).

Hejase, Mohamed J. et al., "Genital Fournier's Gangrene Experience with 38 Patients," Urology, vol. 47:734-739 (1996).

Hill, Dave, "Technical Absorbents.(Expo in Print 2004)," HighBeam Research, retrieved online at http://www.highbeam.com/doc/1G1-117607473.html/print, 3 pages (2004).

M2 Polymer Technologies, Inc., "Super Absorbent Polymer Crystals," retrieved online at http://m2polymer.com/html/super_absorbent_fibers.html, 2 pages (2008).

Molan, P.C. et al., "The Effect of Gamma-irradiation on the Antibacterial Activity of Honey," Journal of Pharmacy and Pharmacology, vol. 48(11):1206-1209 (1996).

Molan, P.C., "The evidence and the rationale for the use of honey as a wound dressing," Wound Practice and Research, vol. 19(4):204-220 (2011).

Molan, P.C., "The Evidence Supporting the Use of Honey as a Wound Dressing," Lower Extremity Wounds, vol. 5 (1):40-55 (2006).

Molan, P.C., "The role of honey in the management of wounds," Journal of Wound Care, vol. 8(8):415-418 (1999).

Seymour, F.I. et al., "Honey—Its role in medicine," Med. Times, vol. 79(2):104-108 (1951).

Subrahmanyam, M., "Honey-impregnated gauze versus amniotic membrane in the treatment of burns," Burns, vol. 20(4):331-333 (1994).

(Continued)

*Primary Examiner* — Abigail Fisher
(74) *Attorney, Agent, or Firm* — Nelson Mullins Riley & Scarborough LLP; Jane E. Remillard, Esq.; Cynthia L. Kanik

(57) ABSTRACT

A composition comprising honey and a super-absorbent material. A method of treating a lesion comprising applying a composition comprising honey and a super-absorbent material to the lesion. A method of manufacturing the composition of the invention, comprising: (a) providing at least one type of honey; (b) providing at least one super-absorbent material; and (c) combining the honey and super-absorbent material.

24 Claims, 2 Drawing Sheets

(56) References Cited

OTHER PUBLICATIONS

Figure 1:
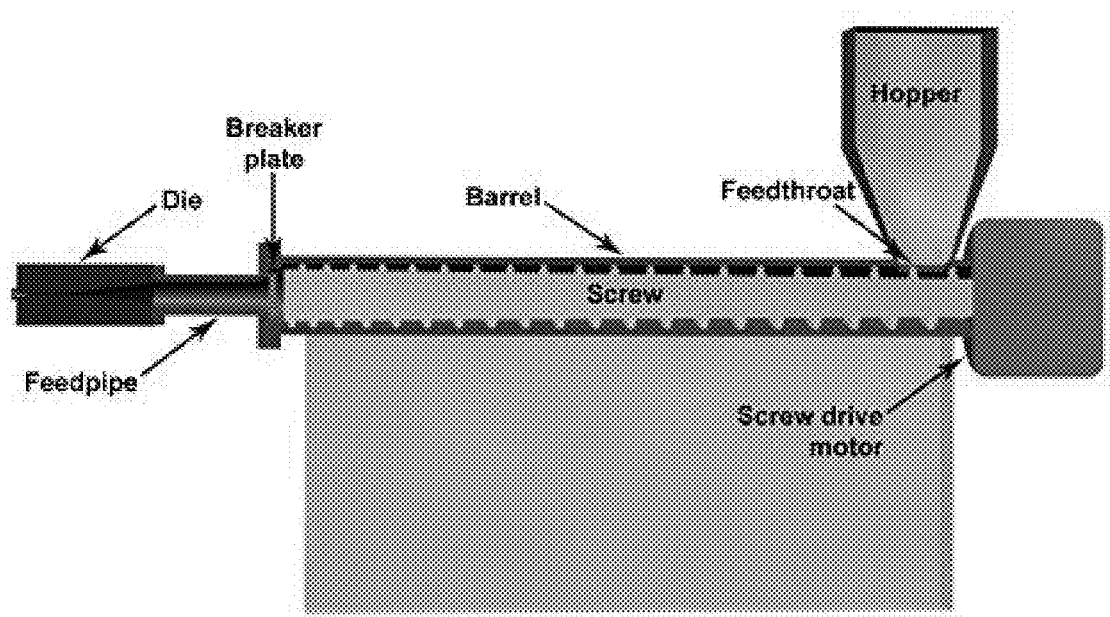

Subrahmanyam, M., "Honey impregnated gauze versus polyurethane film (OPSite) in the treatment of burns—a prospective randomised study," British Journal of Plastic Surgery, vol. 46:322-323 (1993).

European Office Action for Application No. 09757774.6, 6 pages, dated Apr. 4, 2012.

Japanese Office Action for Application No. 2011-512200, 7 pages, dated Aug. 6, 2013.

* cited by examiner

1 Hr 65g (100ml H2O)   1 Hr 61g (100ml H2O)

3 Hrs 75g (100ml H2O)   3 Hrs 75g (100ml H2O)

COMPOSITIONS COMPRISING HONEY AND A SUPER-ABSORBENT MATERIAL

This application is a Continuation of U.S. patent application Ser. No. 12/996,146, filed Apr. 6, 2011, which is a 371 U.S. National Phase Application of International Patent Application No. PCT/GB2009/001407, filed Jun. 5, 2009, which claims priority to British Patent Application No. GB 0810404.4, filed Jun. 6, 2008. The entire contents of each of these patent applications, along with all documents cited therein, are hereby incorporated by reference.

The present invention relates to compositions and more particularly to compositions containing honey which are suitable for use in treating lesions.

The listing or discussion of an apparently prior-published document in this specification should not necessarily be taken as an acknowledgement that the document is part of the state of the art or is common general knowledge.

In the treatment of lesions it is usual for dressings to be applied to the lesion, commonly for prolonged periods. A wide variety of dressings, of numerous different types are in use, and the choice of dressing will depend on a number of factors, including the nature and location of the lesion, the presence or risk of infection and the amount of exudate produced, as well as factors such as the conformability of the dressing and its adhesive properties, and also patient related factors such as the mobility and dexterity of the patient.

The main reasons for the application of a dressing are to facilitate and accelerate healing of a lesion; to prevent malodour, to minimise pain; to prevent and counteract infection; to absorb exudate and to reduce scar tissue.

The healing of lesions is often complicated by infection, making them difficult to treat. Whilst there is a wide range of products used both topically and systemically for clearing lesion infections (including iodine-based preparations and so forth), the main therapeutic intervention for infective lesions, is the use of systemic antibiotics. However, existing antibacterial treatments may have varying effectiveness, and some have been shown to cause tissue damage and slowing down of the healing process. Honey on the other hand, appears to actually promote the healing process with no corresponding tissue damage. Historically, honey has been identified as having healing properties. Recently however, anti-microbial properties of certain honey and their potential use in lesion care have attracted attention.

In New Zealand, the "unique Manuka factor" (UMF) activity identified in Manuka tree-based honey products derived from *Leptospermum scoparium*, and activity identified in other active honey products produced from Australian plant species *Leptospermum polygalifolium* and *Leptospermum subtenue*, has been shown to be useful in relation to infected lesions. Ordinary honey may, nevertheless, also have application for non-infected lesions.

The beneficial properties of some particular honeys, (particularly Manuka honey) include both its anti-bacterial, non-peroxide activity, as well as its peroxide activity. The non-peroxide anti-bacterial activity of these honeys has been shown to inhibit the growth of various species of bacteria and to limit the production of the undesirable bi-products of bacterial growth. Honey with at least 10% non-peroxide activity: (10% phenol equivalent) demonstrates such therapeutic value. Moreover, Manuka honey with at least 12% non-peroxide activity has anti-inflammatory properties, typically reducing pyrogen counts to colony forming units (CFUs) below 5 counts per gram. Manuka honey that has at least 12% non-peroxide activity, has low particulates and slight toxicity (e.g. substantially no toxicity) is referred to as Medical Grade Honey. Such Medical Grade Honey has a low bioburden, for example, as determined by an aerobic plate count.

Whilst the application of honey to lesions is known within the prior art, the use of honey in relation to dressings applied to lesions is still developing.

It is important when a dressing is applied to a lesion that the dressing itself does not stick to the lesion. When the dressing is removed, any healing that may have begun, for example in terms of skin replacement and so forth may be undone where the surface of the skin sticks to the dressing and is removed when the dressing is removed. As can be appreciated this delays the healing process and recovery overall. Moreover, healing processes will not usually occur unless infection is cleared from the lesion.

Honey based products, including UMF honey such as Medical Grade Manuka honey, play a role in managing lesions when applied or used in conjunction with appropriate dressings. Honey based dressings inherently have a number of properties that lend them to use in lesion case. These properties include: a) osmotic absorption of excess exudate; and b) inherent peroxide (antibacterial) activities; which is both lesion cleansing and helps with lesion bed oxygenation; and c) the provision of beneficial nutrients to the lesion bed.

Whilst honey can be applied to an area, the usual fluidity of honey has made localised application difficult. Even the use of absorbent material (such as existing bandages or gauzes), have not successfully addressed inherent difficulties relating to the application of honey to, and its maintenance on, the lesion area. Given that exudating lesions exacerbate this problem the need is identified to produce an appropriate dressing in conjunction with honey in a form that overcomes the above problems.

In addition, to facilitate lesion healing it is preferable that the honey be of a preferred viscosity (whether achieved via specific processing of the honey or not) and/or include concentrated beneficial properties.

It would also be beneficial to make maximum use of the hygroscopic characteristic of honey (capable of absorbing moisture from the air) that provides an advantage to using honey in moist lesion care.

Therefore, it would be advantageous to develop the use of honey-based dressings that may be used: a) in relation to the care of lesions, including non-infected as well as infected lesions; b) to meet the requirements of moist lesion care practices; c) to promote the healing barrier, as opposed to the use of dressings which when removed may delay overall healing; and d) including honey-based products containing higher proportions of active honey and/or honey with preferred properties.

Modern hydro-colloid wound dressings are presently favoured as moist dressings and the use of hydrocolloids in honey based compositions has previously been described. WO 03/047642 discloses wound dressings comprising honey and modified cellulose polymers such as carboxymethylcellulose (CMC), and WO 07/045931 discloses compositions comprising honey and cellulose derivatives such as carboxymethylcellulose and salts thereof. US2006/0099166 describes a honey-based skin preparation, wherein the honey is entrapped within an aqueous polymeric gel based on acrylic monomers or derivatives thereof; however, there is no mention or suggestion of using super-absorbent polymers.

The prior art dressings and compositions have limited capacity to absorb and contain the excess wound exudates that are typical of many wounds. For example, infected wounds and those colonised with bacteria are accompanied by high levels of wound exudates, leakage of which causes damage to the surrounding tissue and newly formed cells.

Therefore, there is a need for dressings that can absorb and contain greater levels of exudate.

Surprisingly and unexpectedly, the inventors have devised compositions comprising honey and superabsorbent material, which combine a high absorption capacity with the therapeutic effects of honey to reduce or eliminate bacterial burden within a lesion and thereby facilitate lesion healing. The super-absorbent material forms a lattice structure that contains the honey. When placed on high exudate lesion wounds, the exudate moves through the super-absorbent material, which may be selectively permeable, due to an osmotic pressure gradient. At the same time, the honey is forced out of the super-absorbent material by displacement as the exudate flows in and disrupts the weaker intermolecular forces holding the honey. The exudate is retained within the swelling super-absorbent material by stronger (hydrogen) bonding. Thus, the composition acts to deliver a controlled release of honey whilst absorbing lesion exudates, which in excess are detrimental to the healing of lesions.

A first aspect of the invention provides a composition comprising honey and a super-absorbent material.

The antimicrobial activity of honey is mediated via: (i) its ability to generate hydrogen peroxide, for example, when added to a site of infection such as a lesion i.e. peroxide based antimicrobial activity; and (ii) plant derived additives in the honey i.e. non-peroxide based antimicrobial activity.

The peroxide based antimicrobial activity in honey is derived from the activity of the enzyme glucose oxidase in all honeys that originate from bees and causes the production of hydrogen peroxide upon dilution at the site of application. This activity is catalase sensitive. Thus, when honey is applied to a lesion its peroxide based antimicrobial activity is attenuated by the enzyme catalase that is produced by tissue at the site of application (e.g. by bacteria) and breaks down the hydrogen peroxide. Peroxide based antimicrobial activity is also particularly sensitive to dilution by body fluids, e.g. blood and serum which contain catalase at the site of infection, that further reduces the antimicrobial activity.

The non-peroxide based antimicrobial activity of honey is derived from plant based additives that are incorporated into the honey during the natural honey making process. These additives are not hampered by the limitations associated with peroxide based antimicrobial activity. Thus, honey with non-peroxide based antimicrobial activity is more desirable as it is more useful for therapeutic purposes, being insensitive to the effects of catalase. Honeys with non-peroxide activity are said to be active and honeys that do not exhibit non-peroxide activity are said to be non-active.

The anti-microbial property of honey is measured in terms of phenol equivalents. The phenol equivalence of honey can be determined using an agar well diffusion method, for example as described in WO 07/009185 and adapted from a punch plate assay for inhibitory substances described in Microbiology Standard Methods Manual for the New Zealand Dairy Industry (1982). Briefly, using a quasi-Latin square as a template, 64 wells are cut in agar sheet seeded with 100 µl of microbes e.g. *Staphylococcus aureus*. To enable the samples to be placed randomly on the plate, the intersections are typically numbered using a white china pencil just above the intersection using a quasi-Latin square. A primary honey solution is prepared by adding 10 g of well mixed honey to 10 ml of distilled water in universals and placed at 37° C. for 30 minutes to aid mixing. To prepare secondary solutions, 1 ml of the primary honey solution is added to 1 ml of distilled water in a bijou for total activity testing and 1 ml of the primary honey solution is added to 1 ml of catalase solution for non-peroxide activity testing (peroxide activity can be determined by subtracting the non-peroxide activity from the total activity). Typically, standards of 2%, 3%, 4%, 5%, 6%, and 7%, are prepared from a 10% w/v solution of phenol BDH A.R. in water, although standards of higher phenol concentration can also be produced. Each standard is placed in, for example, two wells to test in duplicate. After application of samples and standards, the plates are typically incubated on individual racks i.e. not stacked on top of one another, typically for 18 hours at 37° C. The plates are placed back over the black quasi-Latin square to measure the diameter of the zones of inhibition with digital calipers using the points of the prongs used to measure inside diameters of tubes. The mean diameter of the clear zone around each well is calculated and squared. Using the standards, a standard graph is plotted of % phenol against the square of the mean diameter of the clear zone. A best-fit straight line is fitted using, for example, Cricket Graph software and the equation of this line used to calculate the activity of each diluted honey sample from the square of the mean measurement of the diameter of the clear zone. This figure is then multiplied by a dilution factor depending upon the density of the honey to obtain the final equivalent phenol concentration (% w/v). For example, if the density of Manuka honey is assumed to be 1.35 g/ml, this figure would be multiplied by a factor of 4.69.

It is preferred if the honey used in the composition of the invention is active honey, particularly where the composition is used in relation to sites infected by bacteria and so forth. Active honey has been demonstrated to be effective against a broad spectrum of bacteria including gram positive, gram negative, anaerobic and aerobic bacteria. However, non-active honey may also be used either alone, or in combination with active honey.

Active honey requires a 10% phenol equivalent to be of optimum therapeutic value. Accordingly, it is preferred if the honey in the composition of the invention has an anti-microbial activity equivalent to a solution with a phenol content of at least 10%, for example, at least 11%, 12%, 13%, 14%, 15%, 16%, 17%, 18%, 19% or 20%. However, a range of other honeys may also demonstrate active properties to a greater or lesser extent and may also be used with this invention.

Examples of active honeys include those derived from plants of the genus *Leptospermum* (particularly Manuka, Rewa Rewa and so forth) that demonstrate unique non-peroxide activity (anti-microbial activity), as well as peroxide activity (oxygenating and/or cleansing activity). For example, Manuka honey is one type of honey derived from the plant *Leptospermurn scoparium* in New Zealand that has non-peroxide based antimicrobial activity. Similar honeys have been produced from *Leptosperrnum polygalifolium* and *Leptospermum subtenue*.

In a preferred embodiment, the honey is Manuka honey. Manuka is a Maori word that can only be used with the permission of the Maori people. Moreover, the Manuka UMF is governed by the Active Manuka Honey Association (AMHA) and can only be used by AMHA licensed members. Thus, the honey may be UMF® Manuka honey approved by the AMHA. It will be appreciated that Manuka honey is honey that contains pollen from the *Leptospermum scoparium* plant and which exhibits non-peroxide activity, for example equivalent to a solution with a phenol content of at least 10%. However, other active honeys may also be used, preferably having an equivalent phenol concentration of at least 10%, for example at least 11%, 12%, 13%, 14%, 15%, 16%, 17%, 18%, 19% or 20%.

In a particularly preferred embodiment, the honey is Medical Grade Honey which has an equivalent phenol concentration of at least 12%, has low particulates and slight toxicity (e.g. substantially no toxicity). As mentioned above, such Medical Grade Honey has a low bioburden. Medical Grade Honey is typically filtered to 50 mu to remove particles but not pollen and toxicity can be assessed using a cytotoxicity test, for example as described in 1S0 9935 USP 87. In a particularly preferred embodiment, the honey is Medical Grade Manuka honey.

It is appreciated that a number of honeys do not demonstrate active properties, but may nevertheless be used alone or in conjunction with active honey to produce the composition of the present invention, particularly for use with compositions for non-infected moist lesion care purposes. The peroxide activity of non-active honey is highest when freshly harvested. Therefore, it is preferred if the peroxide activity of the honey is approximately similar to that of freshly harvested honey. Preferably, the peroxide activity of the honey is at least 60% of the activity of the freshly harvested honey, for example at least 70%, 80% or 90% of the activity, and more preferably at least 95% or 99% of the activity of the freshly harvested honey.

It will be appreciated that combinations of honeys may be used to produce the composition of the invention. However, the peroxide activity of a non-active honey is believed to degrade rapidly when blended with an active honey due the high concentration of transition metal cations. Accordingly, it is preferred if active honeys are combined with other active honeys, and non-active honeys are combined with other non-active honeys.

By 'super-absorbent material' we mean any material which absorbs and retains aqueous solutions through hydrogen bonding with water molecules and which, in deionised and distilled water, can absorb at least 25 times its dry weight and up to, for example, 800 times its dry weight. The material's ability to absorb water is a factor of the ionic concentration of an aqueous solution. The presence of valent cations in the solution will impede the material's ability to bond with the water molecule. When put in 0.9% saline solution, the absorbency of super-absorbent material typically drops to around 50 times its dry weight. Typically, the super-absorbent material used in the composition of the invention absorbs at least 25, 50, 75, 100, 150, 200 or 250 times its dry weight when in deionised and distilled water and more typically at least 300, 350, 400, 450, 500, 550, 600, 650, 700, 750 or 800 times its dry weight. It is preferred if the super-absorbent material absorbs at least 25, 50, 75, 100, 200 or 250 times its weight when on a lesion bed. A suitable test for determining whether a material is super-absorbent is the AATCC Test Method 79-2007, Absorbency of Textiles.

Preferably, the super-absorbent material is a super-absorbent polymer (SAP).

SAPs are commonly made from the polymerization of acrylic acid blended with sodium hydroxide in the presence of an initiator to form a poly-acrylic acid, sodium salt (sometimes referred to as cross-linked sodium polyacrylate). However, other monomers may also be used. For example, OASIS Super-absorbent fibre (OASIS SAF®) is a cross-linked terpolymer of acrylic acid, methylacrylate and a small amount of a special acrylate/methacrylate monomer (SAMM) in which the acrylic acid is partially neutralized to the sodium salt of acrylic acid. The cross-links between the polymer chains are formed as ester groups by reaction between the acid groups in the acrylic acid and the hydroxyl groups in the hydroxypropylmethacrylate.

SAPs suitable for use in the present invention include cross-linked sodium polyacrylate, polyacrylamide copolymer, ethylene maleic anhydride copolymer, cross-linked carboxy-methyl-cellulose, polyvinyl alcohol copolymer, isobutylene-maleic anhydride copolymer, cross-linked polyethylene oxide, starch grafted copolymer of polyacrylonitrile and OASIS SAF®.

Preferably, the SAP is a polymer of neutralised acrylic acid such as sodium polyacrylate, polyacrylamide copolymer and OASIS SAF®. OASIS SAF® has the appearance and improved handling characteristics of a textile fibre whilst offering the possibility of producing very soft handle fabrics. It is white, odourless and has a very similar chemistry to Absorbent Granular Materials (AGM). Compared with such granular absorbents, OASIS SAF® offers benefits in ease of handling, containment and processing routes available. In a particularly preferred embodiment, the SAP is OASIS SAF® available from Technical Absorbents Ltd, Grimsby, Lincs, UK (Product Reference 2577) which weighs 150 g/m² at about 2 mm thick, but any OASIS SAF® type may be used and it is noted that types are available that weigh between 100-350 g/m².

Methods of producing SAPs are well known in the art and any suitable method may be used. Generally, the polymers are produced either by solution polymerisation or suspension polymerisation. Solution based polymerisation, the most common method, uses a water based monomer solution to produce a mass of reactant polymerised gel. The polymerisation's own reaction energy (exothermic) drives much of the process, thereby minimising manufacturing costs. The reactant polymer gel is chopped, dried and ground to its final particle size. Any treatments to enhance performance characteristics of the SAP are carried out after the final particle size is created. Suspension polymerisation offers a higher degree of production control and product engineering during the polymerisation step. This process suspends the water based reactant in a hydrocarbon based solvent. The net result is that the suspension polymerisation creates the primary polymer particle in the reactor rather than mechanically in post-reactions stages. Performance enhancements can be introduced during or just after the reaction stage.

In addition to particles, SAPs may also be produced as fibres. The manufacture of OASIS SAF® comprises polymerisation in water followed by extrusion of the aqueous polymer solution in a hot air stream to dry and cure the polymer, thereby producing insoluble polymer fibres. An extremely high conversion rate of the raw materials to polymer is achieved. Moisture may be added to the fibres to aid processing, and the fibres are precision cut into a range of staple lengths. The OASIS Super Absorbent technology can also be used to produce filament yarns (OASIS-FIL) and polymer solutions (OASIS-PS), either of which may be used in the composition of the invention.

The total absorbency and swelling capacity of SAPs are controlled by the type and degree of cross-linking to the polymer. A low density cross-linked SAP generally has a higher absorbent capacity and swells to a larger degree. These types of SAPs also have a softer and more cohesive gel formation. High cross-link density polymers exhibit lower absorbent capacity and swell. The gel strength is firmer and can maintain particle shape even under modest pressure. Depending upon the required absorbency of the composition, both low and high density cross-linked SAPs may be used. Thus, when the composition is used to treat lesions with high volumes of exudate, low density cross-linked SAPs are preferred, whereas for lesions which produce minimal exudate, high density cross-linked SAPs may be used.

For ease of application to a lesion it is preferred if the composition is in the form of a semi-solid pliable sheet, that is the sheet is flexible. For example, the composition may be moulded or plied into shape by finger pressure, or it may simply be draped across and conform to the shape of the area covered by the dressing. Preferably, the composition is such that it can be in intimate contact with the surface of a lesion in order to effect preferred healing. To test whether the composition is semi-solid pliable, the cantilever beam test developed to assess the drape of textile materials may be used as is well known in the art. In this test, the drape is measured through the length of fabric that will bend under its own weight when held out over an edge. The less a material will be able to support itself the more pliable it will be. Typically, a pliable sheet will be able to support no more than, for example, 15 mm of sheet placed over an edge. More recently designed three-dimensional measuring techniques may also be used to determine pliability as are known in the art.

By 'sheet' we include the form of a film, a strip, a patch or a rope.

The honey may be combined with the super-absorbent material to form the semi-solid pliable sheet. For example, a pliable sheet of SAP and honey can be produced by warm extrusion. In one method of manufacture, a SAP and honey can be combined via hopper feeds into the feed throat (an opening near the rear of the barrel) where they are mixed, for example by coming into contact with a screw which effectively mixes the ingredients. A suitable extruder is illustrated in FIG. 1. It is desirable to have positive feed controls to regulate the mixture. The screw typically rotates at 120 rpm and forces the mixture forward into the barrel which is heated to the desired process temperature for the honey (typically between 35° C.-50° C., for example 35° C.-45° C.). The heating profile is normally set for the barrel in which three or more independent PID controlled heater zones gradually increase the temperature of the barrel from the rear (where the mixture enters) to the front. Temperature regulation in the barrel can be by forced air cooling cast-in heater jackets, and a closed loop of distilled water in heat exchange with tower or mains water is often used. After passing through the barrel the mixture enters the die. The die gives the final product its profile and is designed so that the mixture evenly flows from a cylindrical profile, to the product's profile shape. The product is then cooled, for example by heat exchange or blown cold air. The cooling may also be achieved by pulling the product through a set of cooling rolls (calender rolls). These rolls not only deliver the necessary cooling but also determine sheet thickness and surface texture (in case of structured rolls). It is also possible immediately prior to the cooling stage/calendering stage to combine the mixture with a suitable material for reinforcing the structure e.g. a non-woven, woven, knitted or other textile material of synthetic or natural origin or a polymer film e.g. polyurethane, polypropylene or polyethylene film.

Alternatively, a semi-solid pliable sheet comprising super-absorbent material may be impregnated with the honey.

The sheet to be impregnated with honey may be a layered structure. For example, it may comprise at least one layer of a cellulose compressed material (e.g. tissue paper) interspersed with at least one layer of super absorbent particles (for example super-absorbent powder or crystals). Typically, tissue paper is used which weighs between 10-35 g per square meter. However, other suitable materials may be used to provide a support layered structure in which the super-absorbent particles are interspersed, such as, for example, polyester. The number of layers would typically determine the absorbent capacity of the sheet given the same degree of cross-linking of the same monomers.

An example is Gelok available from Gelok International, P.O. Box 69, Pine Lake industrial Park, Dunbridge, Ohio 43414-0069 USA. Gelok products consist typically of a composite polyacrylate laminate structure—a superabsorbent polymer base between two cellulose sheets. The degree of absorbency is determined by the amount of polymer used. Other materials may be added to the core to produce a variety of new performance characteristics. The substrate characteristics can also be varied by the use of other materials, such as airlaid tissue for natural biodegradation (flushability) or polyester nonwovens for durability.

Alternatively, the sheet to be impregnated with honey may be a non-layered structure. For example, the sheet may comprise super-absorbent material and cellulose fibres in a non-layered structure. The production of such a sheet structure is described in EP0255654 and comprises the steps of: (a) forming a suspension, in an air stream, of an intimate mixture of cellulose fibres and super-absorbent polymer; (b) feeding said suspension to a single or multiple head for dry-forming sheets of paper; (c) laying-down said intimate mixture of cellulose fibres and super-absorbent polymer onto a moving web for dry-forming sheets of paper; and (d) binding together the thus laid-down layer of fibres and polymer by means of a resin dispersion, of the type which is used for the dry-formation of paper sheets, and calendering it so as to dry-form a sheet constituted by a mixture of super-absorbent polymer and cellulose fibres. Such sheets have characteristics of absorbency, resistance and distributing of the absorbed liquids, which are considered better than those of composite sheets comprising a layered structure. However, because the cellulose fibres absorb fluid in addition to the SAP, these sheets are generally more wet and so are not as preferred as the layered sheets described above, in the context of treating lesions.

The honey may be impregnated by continuous (roll to roll) dip coating. In this method, a roll of the super-absorbent sheet pre-cut to a desired width is drawn through an immersion tank of warm honey (typically between 35° C.-50° C., for example 35° C.-45° C.), typically at a constant speed after which it is wound into a roll. It is appreciated that the sheet to be impregnated need only be just beneath the surface in the tank of honey. Blades to remove excess honey are combined with a nip roller to create a constant pressure at the point of exit from the tank. The degree of impregnation of the sheet with the honey is determined by the submersion time and the time under roller pressure. It is therefore important to regulate the honey level within the tank and time under roller pressure. The level of honey in the tank is maintained by pumping more honey into the bath when the level is reduced. Typical dwell times are in the region of 2-6 seconds depending on the material being impregnated. The speed is determined by the tensile strength along the length of the material. After leaving the tank and passing the nip rollers the impregnated sheet is dried before being wound into a roll form. The roll is further processed into cut lengths for use as a wound dressing. It will be appreciated that other methods of impregnation may also be used such as, for example, batch process of emersion.

Typically, the thickness of the composition when in the form of a sheet ranges from 0.25 mm to 10 mm; for example, the sheet may be 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm or 10 mm thick. Preferably, the sheet is less than 5 mm, 4 mm or 3 mm thick and more preferably less than 2 mm thick.

The honey is preferably combined with the super-absorbent material such that the honey does not saturate the super-absorbent material, thereby leaving capacity for absorbing lesion fluid components. Saturation is defined as the point at which the super-absorbent material no longer gains weight upon addition of fluid. Thus, honey would saturate the superabsorbent material, if upon addition of further honey the material did not gain anymore weight. It is appreciated that the super-absorbent material becomes a gel only when its capacity to absorb more fluid is completely used. Preferably, the honey utilises between 5% and 50% of the super-absorbent material's absorbent capacity, such as 10%, 15%, 20%, 25%, 30%, 35%, 40% or 45% of the material's absorbent capacity. In a particularly preferred embodiment, the honey utilises less than 10% of the material's absorbent capacity, for example 9%, 8%, 7% or 6% of the material's absorbent capacity. Absorbent capacity is typically measured in terms of the maximum dosage rate that leads to saturation. For example, for a given piece of super-absorbent material, if 10 g honey is the maximum dosage rate, 50% of the material's absorbent capacity would be utilised when 5 g honey is contained. Comparing the absorbent capacity of an impregnated sheet comprising super-absorbent material with that of the non-impregnated sheet can also be used to assess the utilisation of absorbent capacity.

In any event, it is appreciated that the honey is combined with the super-absorbent material such that the honey does not utilise all of the super-absorbent material's capacity to absorb fluid. Typically, the honey coats the super-absorbent material (eg fibres) and reduces the absorbency rate but as honey is diluted by exudates for example, the capacity for absorption is restored.

Preferably, the honey is combined with the super-absorbent material such that the super-absorbent material is able to absorb at least 10 times its dry weight when in water, and more preferably at least 20, 30 40 or 50 times its dry weight. For example, when honey is combined with a super-absorbent material in a weight ratio of 4:1, the super-absorbent material typically absorbs 10 times its dry weight when in water.

The ability of a super-absorbent material to hold honey within its structure is dependent on the mass, density and type of the material and the impregnation method used. The weight ratio of honey to super-absorbent material largely depends on the area/size of the sheet of the composition. A typical dosage of honey which does not lead to saturation is 0.2 g/cm$^2$, and so for a 5 cm×5 cm sheet the dosage would be 5 g honey and for a 10 cm×10 cm sheet the dosage would be 20 g honey. Thus the sheet may contain between 0.1 g/cm$^2$ and 0.3 g/cm$^2$ such as between 0.15 g/cm$^2$ and 3 g/cm$^2$. However, it will be appreciated that other dosages outside this range may be used which give the required utilisation of absorbent capacity, depending upon the super-absorbent material used and the thickness of the sheet.

Typically, the weight ratio of honey to super-absorbent material is at least 2:1 such as at least 3:1, 4:1, 5:1, 6:1, 7:1, 8:1 and 9:1, and more typically at least 10:1, such as at least 15:1, 20:1, 25:1 and 30:1. However, it is appreciated, for example when the super-absorbent material is in a powder form, that the weight ratio of honey to super-absorbent material may be up to 40:1 or 50:1, and even up to 100:1, 150:1 or 200:1.

The composition may comprise further agents. For example, the compositions may further comprise any one or more of a pharmaceutical, a gelling agent, a viscosity altering agent e.g. glycerine, a vitamin, a hormone, an antibiotic, a cation, or a plant extract. Where additional agents are added, it will be appreciated that such factors regarding the suitability for medical or intended use, stability over time, compatibility with honey and the ability to form the composition having the desired physical and therapeutic properties must be considered. Such factors will of course be dictated by the requirements of use of the intended purpose.

We have shown that when a composition comprising a honey and a super-absorbent material is in contact with wound fluid, the fluid is absorbed and honey will be released into the wound. Thus, the composition can be used to deliver a controlled release of honey while absorbing exudates from lesions that in excess are detrimental to healing. Moreover, honey and in particular active honey is known to have antimicrobial properties such that the composition of the invention is believed to be effective against infections caused by, for example, *Staphylococcus* such as *S. aureus* and methiciliin resistant *S. aureus* (MRSA), *Enterococcus* including vancomycin resistant *Enterococcus* (VRE), *Escherichia* such as *E. coli*, *Pseudomonas* such as *P. aeruginosa*, *Acinetobacter* such as *A. baumarii*, *Helicobacter* such *H. pylori* and *Neisseria* such as *N. meningitides*. Antibiotic resistant bacteria are considered to be particularly amenable to treatment using the compositions of the invention.

It is desirable that a honey containing composition can be placed directly into contact with a lesion such that a moist wound environment, known to be favourable to healing, is maintained. However, combining honey with matrix material such as fibres (eg in a dressing) results in a sticky product that is difficult to handle. For example, alginate dressings or other gel forming fibre dressings impregnated with honey such as Algivon from Advancis Medical and Api-Nate from Comvita, or any fibrous dressing (eg Gamgee from Robinson Healthcare and Aquacel from Convatec) to which honey is applied directly prior to application, are sticky and difficult to handle. Further, where the fibres within a honey containing composition are mixed eg superabsorbent-polymer fibres and Polyester (OASIS® SAF) or consist entirely of non-gelling fibres, (eg polyester, polyamide or polypropylene), the non-gelling fibres have a tendency to adhere to the lesion bed when the honey is sufficiently diluted by exudates. This is most likely to happen when the lesion starts to dry out which is normal during the healing process. Removal of an adhered dressing can be painful and new tissue formation is disrupted by the loss of cells, thereby disrupting and delaying healing of the lesion.

The inventors have now demonstrated that by coating the surface of compositions comprising honey and a matrix material (eg honey impregnated fibre dressings) with a gelling agent, a dryer, less sticky and more easy to handle composition is produced which overcomes the issue of adherence of non-gelling fibres to a wound. The gelling agent coating creates a surface of gelled material which reduces the potential for such compositions (eg honey impregnated fibre based dressings) to adhere to a lesion bed. The gelling agent is held onto the surface of the honey containing composition by the stickiness of the honey, and forms a barrier minimising exposure of honey on the surface such that the composition is less sticky and easier to handle.

Accordingly, a second aspect of the invention provides a composition comprising honey and a matrix material, which composition is coated with a gelling agent.

On a lesion bed the coat of gelling agent initially absorbs the exudates and forms a non-adherent gel layer on the surface of the composition. As the gelling agent is permeable it does not prevent the absorbance of fluid into the composition but may reduce the absorption rate. Such delayed absorption may be advantageous in that it reduces the rate of displacement of honey and prolongs the potential wear time of the composition. Honey diffuses into the gel layer formed by the gelling agent and exudate and is made available to the lesion in a gel form. This active surface gel may be considered as a honey gel or hydrocolloid-honey gel.

Preferences for the honey are as defined above with respect to the first aspect of the invention. The honey is preferably an active honey such as Manuka honey and is typically Medical Grade Honey.

By 'matrix material' we include the meaning of any material which can hold the honey together in a form that can be used to treat lesions. Typically, the matrix material holds the honey together in a solid or semi-solid form.

Thus it will be appreciated that the composition comprising honey and a matrix material is one which is suitable for use as a lesion dressing. For example, it may be a honey impregnated dressing, in which case the matrix material may be any material that is suitable for use in dressings.

The matrix material may be any non-woven (eg felt), woven, knitted or other textile material of synthetic or natural original or a polymer film e.g. polyurethane, polypropylene or polyethylene film. It may contain either or both of a gelling material (eg fibre such as super-absorbent polymer) and a non-gelling material (eg fibre such as polyester, polyamide or polypropylene). In a particularly preferred embodiment, the matrix material is alginate and more preferably gauze (eg knitted viscose gauze).

In an embodiment, the composition of the second aspect of the invention comprising honey and a matrix material is the composition of the first aspect of the invention coated with a gelling agent. Thus, the invention provides a composition comprising honey and a super-absorbent material, which composition is coated with a gelling agent. However, any composition comprising a matrix material and honey may be coated with a gelling agent such as any of the above matrix materials impregnated with honey.

As for the composition of the first aspect of the invention, it is preferred if the composition of the second aspect of the invention is in the form of a sheet. Preferably, the sheet is a semi-solid pliable sheet that may be used as a conformable lesion dressing.

By 'coated' we include the meaning that the surface of the composition is covered with a layer of gelling agent. Preferably, the composition is evenly coated with a gelling agent.

Typically, the layer of gelling agent is less than 500 µm thick, more typically less than 400 µm, 300 µm, 200 µm or 100 µm thick and yet more typically less than 50 µm, 40 µm, 30 µm, 20 µm, 10 µm, 5 µm, 1 µm or 0.1 µm thick.

By a 'gelling agent' we include the meaning of an agent which, in the absence of liquid is not a gel, but which agent is able to form a gel in the presence of liquid. In this way, upon exposure to liquid such as exudate, a gel layer will be formed on the surface of the composition which will reduce the potential for the composition to adhere to a lesion bed. Gelling agents are typically used in the food, pharmaceutical and cosmetic industries to control the consistency or physical properties of preparations (eg to thicken food), and it is appreciated that any such agent may be used in the context of the present invention. Preferably, the gelling agent is a hydrophilic gelling agent.

Conveniently, a coefficient of friction (COF) is used to compare uncoated (i.e. not coated with a gelling agent) (UM) with coated (i.e. coated with a gelling agent) (CM) compositions comprising honey and matrix material, as is well known in the art. For example, a UM placed on a sheet of glass and inclined at 45 degrees will remain static due to the stickiness of the honey whereas a coated material would slide off the glass. Coating with a gelling agent will typically reduce the COF by at least 10 times and more typically by at least 50 or 100 times. The COF of both UMs and CMs will change after absorption of liquid but the rate of change is relative to the nature of the matrix material and the amount of liquid being absorbed. However, the CM will reduce its COF quicker than the UM due to the surface gelling effect acting as a lubricant. As absorption progresses with time, the honey is diluted within the matrix and the COF changes. Depending on the matrix materials, the COF differential of UMs and CMs will either equalise (in the case of gelling fibre matrixes) or increase e.g. a gauze dressing will increase its COF when the honey is diluted by exudates as the honey itself acts as a lubricant on the fibres. It will be appreciated that in the absence of either honey or gelling agent, a non-gelling matrix material has the potential to provide a matrix for new cell growth which causes it to become integrated with the new tissue. This is apparent when a dressing becomes stuck to a lesion bed making it hard to remove. To facilitate removal of a dressing that has adhered to a lesion bed it is often necessary to rehydrate the dressing (e.g. with sterile saline solution).

Particular examples of gelling agents include carrageenan derivatives, cellulose polymers, super-absorbent polymers, alginates and hydro-fibres. Preferably, the gelling agent is a cellulose polymer, and most preferably, the gelling agent is carboxy-methyl-cellulose.

It will be appreciated that the gelling agent may take any form such as a powder or a sheet or a granule.

Conveniently, the gelling agent is a powder or granule such as a super-absorbent polymer, alginate or carboxy-methyl-cellulose powder, which can readily coat the surface of the honey containing composition.

Any suitable method known in the art may be used to coat a composition of the invention with a gelling agent powder or granule. Preferably, a continuous coating method is used. One method for surface coating is a simple 'dusting' machine apparatus, a hopper is filled with the desired coating powder or granule and the powder or granule is delivered through a sieve (mesh) that is agitated to deliver the powder or granule at constant rate. The coating weight is controlled by varying the speed at which the composition (eg impregnated material) passes under the sieve. A series of rollers can turn the composition (eg impregnated material) through 180 degrees and a second dusting head provided to coat the other side of the composition. Another coating method is the transfer of powder or granule from a hopper via gravure rollers which will deliver a controlled amount of powder or granule as the rollers rotate. This can also be applied either side of a composition. Alternatively, a powder or granule spray method may be used whereby the powder or granule is sprayed onto the composition (eg impregnated material).

Alternatively, the gelling agent may be a sheet, for example a sheet of a gel forming polymer such as carboxy-methyl cellulose, or a sheet of a combination of polymers and additional gelling agents (eg alginate). Such sheets are available from BioFilm Limited, Glasgow, UK.

When in the form of a sheet, a composition of the invention may be coated with a gelling agent sheet, for example by a laminating process wherein the sheet of gelling agent is deposited onto the honey containing composition sheet and adheres to the surface due to the sticky nature of the honey.

Preferably, coating a composition comprising honey and a matrix material with a gelling agent reduces stickiness and improves handling for a period of at least 1, 2, 3, 4, 5 or 6 months after coating, such as at least 7, 8, 9, 10 or 11 months and more preferably at least 1, 2, 3, 4, 5 or 6 years after coating.

As discussed above, it is appreciated that the compositions of the invention can be used to deliver a controlled release of honey to lesions.

Accordingly, a third aspect of the invention provides a dressing comprising the composition of the first or second aspect of the invention. It will be appreciated that such dressings are suitable for treating lesions.

By 'dressing' we include any covering that can be applied to a lesion. By 'lesion', we include infected and non-infected abrasions, cuts, bites, burns, wounds, ulcers, abscesses, surgical wounds, fungating tumours and pressure sores. The lesion is preferably external, for example resulting from damage or injury to the skin.

Preferably, the dressing is a semi solid covering, for example one which is pliable, flexible and conformable for ease of application to lesions.

Typically, the dressing comprises the composition of the first or second aspect of the invention, preferably in the form of a sheet (eg a semi-solid pliable sheet), encased within a fluid permeable material, i.e. one which does not demonstrate resistance to the penetration of fluid. Typically, the dressing is encased between two sheets of fluid permeable material that are joined together on all sides.

The fluid permeable material may be any non-woven, woven, knitted or other textile material of synthetic or natural origin or a polymer film e.g. polyurethane, polypropylene or polyethylene film. Non-woven fabric is typically manufactured by putting small fibres together in the form of a sheet or web, and then binding them either mechanically (as in the case of felt, by interlocking them with serrated needles such that the inter-fiber friction results in a stronger fabric), with an adhesive, or thermally (by applying binder (in the form of powder, paste, or polymer melt) and melting the binder onto the web by increasing temperature).

Preferably, the fluid permeable material is a polymer based non-woven material such as polyester, polyurethane, polypropylene or polyethylene. Non-woven materials are preferred since they are commonly used in absorbent dressing pads, are more economical, easily heat welded and readily available in a wide range of weights and surface treatments. Moreover, a non-woven material with a suitably heat calendared finish exhibits low adherence to a lesion bed. However, woven fabrics may also be used.

The fabric density of the fluid permeable material is preferably in the range of 100 to 200, for example 150 to 180 gsm ($gm^{-2}$), although use of a lighter or heavier fabric may be possible. However, it will be appreciated that with lighter weight fabrics, for example of 70 gsm or less, it may be more difficult to produce dressings substantially impervious to liquid.

It is preferred if the dressing is substantially impervious to liquid water but permeable to water vapour. By 'impervious' we mean that liquid water (or aqueous liquid such as saline solution) does not penetrate all the way through the structure and emerge at the opposite face. Thus, liquid water may pass through one side of the dressing and moisture vapour emerge from the other side of the dressing. This can be tested by subjecting the dressing to a "Paddington Cup test" (as described in the 1996 Addendum to the British Pharmacopoeia, p 1943), in which a saline solution is applied to the upper surface of a sample sheet clamped between a pair of flanges and it is determined whether the saline passes through the sheet within 24 hours. Specifically, it is preferred if the dressing is capable of achieving a 24 hour moisture-vapour transmission rate of at least 600 g per 100 $cm^2$ and a 24 hour total fluid handling capacity of at least 500 g per 100 $cm^2$.

In this way, the dressing will be suited for use as a moist lesion dressing which assists in the healing of exuding lesions since it retains its structural integrity in moist conditions, is able to form a barrier to liquid water, and yet both absorbs liquid water and transmits substantial amounts of water vapour at a steady rate. Both liquid absorbency and vapour transmission are important in lesion healing. Absorbed liquid will include other lesion fluid components and debris, as well as water. Moisture vapour transmission is an ongoing property of the dressing where liquid absorption (absorbency) is a property which attains a maximum level.

When the dressing is one that comprises a composition coated with a gelling agent, it will be appreciated that there is no need for it to be encased within a fluid permeable material, since handling of the composition will be much improved.

To hold the dressing in place, the dressing typically comprises additional elements such as bandages (flat or tubular), cohesive bandages, tapes and/or adhesive strips, integral with or used in conjunction with the dressing. For example, the dressing may comprise an adhesive border. It will be appreciated that the dressing may comprise such additional elements whether or not it is encased in a fluid permeable material.

Where the lesion has minimal exudate, it is preferred if the dressing comprises a non-adherent contact layer between the lesion bed and the semi-solid pliable sheet.

For application to a lesion, it is important that any composition or dressing is sterile in order to avoid the risk of infection. Thus in one embodiment, the composition or dressing of the invention are sterile. Any sterilisation method may be used as is known in the art; for example, gamma irradiation or electron-beam irradiation may be used. Typically, the dressing is irradiated by 25 kGy or more, or by lower amounts sufficient to achieve sterilisation. In a further embodiment, the composition or dressing of the invention is contained within a sterile packet.

In one embodiment, the composition or dressing of the invention comprises a liner (eg a plastic liner such as low density polyethylene (LDPE)) applied to one or both sides to facilitate aseptic handling of the dressing. In this way, there is less need to directly handle the dressing when placing it onto a lesion and potential contamination of a sterile dressing or composition is reduced.

However, it is appreciated that liners may not always be required for compositions coated with a gelling agent, provided that good aseptic technique is adopted, since these compositions are easier to handle directly.

It will be appreciated that the compositions and dressings of the invention are preferably biocompatible. By 'biocompatible' we mean that the compositions or dressings do not elicit any undesirable local or systemic effects in the recipient thereof. For example, the composition or dressing should not have any toxic or injurious effects.

A fourth aspect of the invention provides a composition according to the first or second aspect of the invention or a dressing according to the third aspect of the invention for use in medicine.

A fifth aspect of the invention provides a method of treating a lesion, comprising applying the composition according to the first or second aspect of the invention or dressing according to the third aspect of the invention to the lesion.

The invention also includes the use of a composition according to the first or second aspect of the invention or dressing according to the third aspect of the invention in the manufacture of a medicament for treating a lesion.

The invention also includes a composition according to the first or second aspect of the invention or dressing according to the third aspect of the invention for use in treating a lesion.

A sixth aspect of the invention provides a method of manufacturing the composition according to the first aspect of the invention, comprising:

(a) providing at least one type of honey;
(b) providing at least one super-absorbent material; and
(c) combining the honey and super-absorbent material.

Preferences for the honey and the super-absorbent material are as described above with respect to the first aspect of the invention.

In one embodiment, step (c) comprises combining the at least one type of honey and the at least one super-absorbent material to form a dressing in the form of semi-solid pliable sheet as described above. Typically, the honey and super-absorbent material are combined to form the sheet by the warm extrusion method described above, however it will be appreciated that a cold extrusion method may also be used.

In an alternative embodiment, step (c) comprises impregnating a semi-solid pliable sheet comprising at least one super-absorbent material, with at least one type of honey. The semi-solid pliable sheet comprising at least one super-absorbent material may be any such sheet. For example, the sheet may comprise layers of a cellulose compressed material or layers of polyester interspersed with super-absorbent particles, or it may comprise a mixture of super-absorbent material and cellulose fibres in a non-layered structure, as described above. Typical methods of impregnating the sheet with the honey are also as defined above.

Preferences for the composition of the semi-solid pliable sheet such as its thickness are defined as above with respect to the first aspect of the invention.

In order to preserve or maintain any of the active properties of the honey used in the honey composition, it will be appreciated that temperatures involved in the manufacturing of the composition should preferably be maintained at low-levels (or at high temperatures for a very short period(s) of time). Prolonged exposure to high temperatures destroys the active properties of active honey. Thus, typically the honey and super-absorbent material are combined at temperatures between 35° C. and 50° C., for example between 35° C. and 45° C. It will be appreciated that where the composition contains one or more viscosity reducing agents, e.g. glycerine, relatively low temperatures may be used. However, where viscosity is high, relatively high temperatures may need to be used in order to achieve a uniform composition.

A seventh aspect of the invention provides a method of manufacturing a composition according to the second aspect of the invention, comprising coating a composition comprising honey and a matrix material with a gelling agent.

Preferences for the composition comprising a honey and a matrix material and the gelling agent are defined as above with respect to the second aspect of invention, as are typical methods of coating the composition with a gelling agent.

When the dressing of the third aspect of the invention solely comprises the composition of the first or second aspect of the invention it will be appreciated that its method of manufacture is the same as that of the composition. However, when it does not, further steps are necessary.

Accordingly, an eighth aspect of the invention provides a method of manufacturing the dressing according to the embodiment of the third aspect of the invention wherein the composition is encased, the method comprising:

(a) providing the composition of the first or second aspect of the invention; and
(b) encasing the composition within a fluid permeable material.

Preferably, the composition is in the form of a sheet (eg a semi-solid pliable sheet).

Preferences for the fluid permeable material are as defined above with respect to the second or third aspect of the invention.

Encasing the composition typically involves enclosing the composition of the first or second aspect of the invention when in the form of a semi-solid pliable sheet, by a fluid permeable material to form a sachet. This can be achieved by placing a sheet of the composition centrally between two layers of fluid permeable material e.g. non-woven material, allowing a sufficient border for welding the material on all sides to form a sachet containing the composition. Welding can be achieved by a number of methods but most likely thermal or ultrasonic means. It will be appreciated that this process can be carried out on a continuous basis with roll fed fluid permeable materials, e.g. nonwovens and manual or robotic placement of the composition sheets. After sealing the edges the sachets may be separated by a cutting process. It is preferable that different fluid permeable materials e.g. different nonwovens form the two sides of the sachet. Preferably, the side of the sachet that will be in intimate contact with the lesion is lightweight and highly fluid permeable to allow rapid penetration of lesion exudates. The material on the opposite side, i.e. the backing material is preferably a laminated fluid permeable material e.g. nonwoven material with an ability to allow the passage of moisture and vapour but is resistant to the passage of fluid. The backing material can alternatively be entirely polymer based. In this way, it will be appreciated that the different fluid permeable materials forming the two sides of the sachet may have different degrees of fluid permeability. For example, the material forming the side of the sachet in contact with the lesion may have a higher fluid permeability (eg it may be liquid permeable) than the fluid permeability of the backing material (eg which may be permeable only to vapour).

In an embodiment, the method further comprises coating the dressing with an adhesive suitable for contact with the skin. For example, when the dressing is in the form a sachet described above, the sachet backing may be coated with an adhesive and the backing material may overlap with the lesion contact material on all sides. Typically, there will be in the region of a 1 cm-5 cm overlap and most typically 2-3 cm. This type of dressing with an adhesive border on all sides is commonly referred to as an island dressing. Any suitable adhesive may be used, including for example, an acrylic adhesive or silicone adhesive.

In an embodiment of the sixth, seventh and eighth aspects of the invention, the method further comprises sterilising the composition or dressing, for example by gamma irradiation or electron beam irradiation.

In another embodiment of the sixth, seventh and eighth aspects of the invention, the method further comprises containing the composition or dressing within a sterile packet.

The invention provides a dressing comprising OASIS SAF 2577® impregnated with Manuka honey, dusted with carboxy-methyl-cellulose.

The invention provides a dressing comprising knitted viscose gauze impregnated with Manuka honey, dusted with carboxy-methyl-cellulose.

The invention will now be described in more detail with the aid of the following Figures and Examples.

FIG. 1: Cross-section of an extruder that may be used to combine a honey with a super-absorbent material to form a semi-solid pliable sheet.

Figure 2:
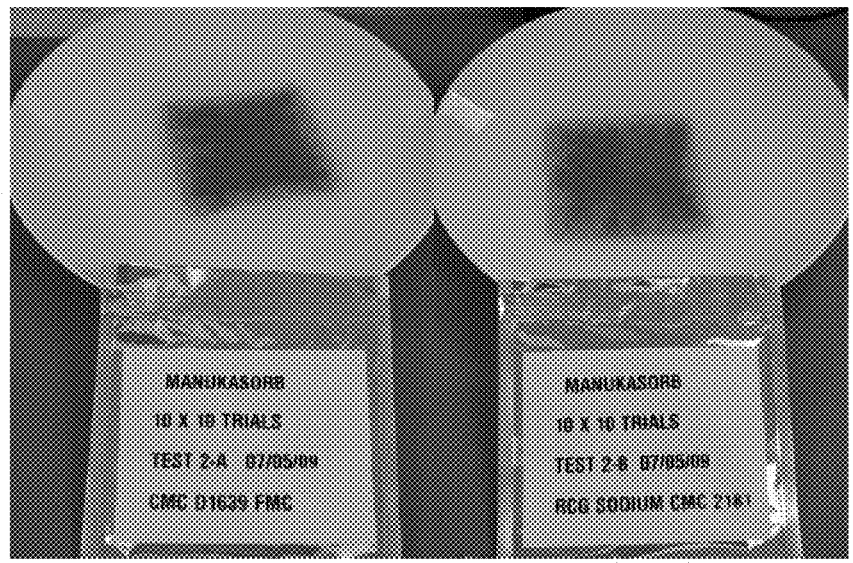
Figure 2:
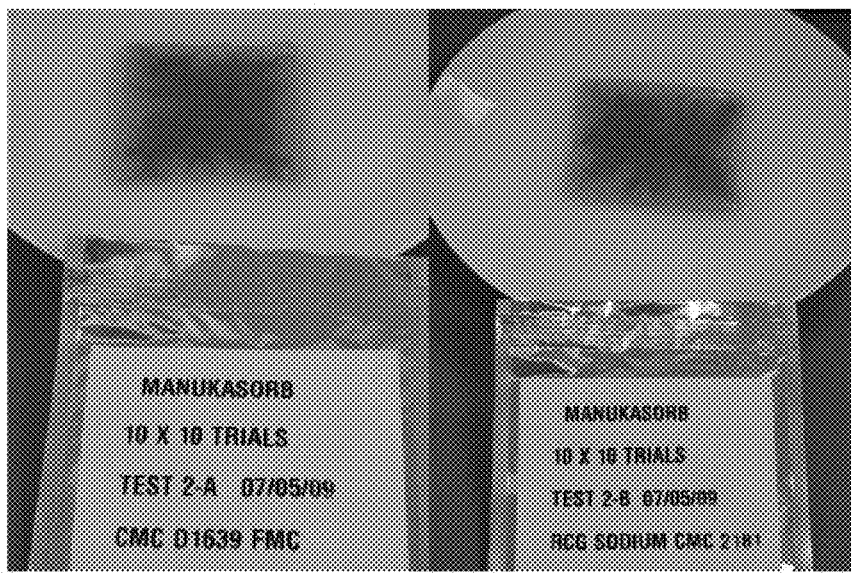

FIG. 2: Gelling and absorption properties of CMC coated honey/super-absorbent compositions.

EXAMPLE 1

Using a Honey/Super-Absorbent Material Dressing to Treat Wounds

The dressing of the invention is placed face down onto a lesion surface; dressings can be placed side-by-side to cover large wound areas. If minimal exudate is present, a non-adherent lesion bed contact layer should be used in between the honey/super-absorbent material composition sheet and the lesion bed. Depending on the tissue type within the lesion bed and the exudate levels, the fixation method of choice could be a flat or tubular bandage, a cohesive bandage and/or suitable tape. The dressing may be used beneath compression therapy.

Depending on wound exudate levels, any surrounding interstitial fluid and oedema, the dressing may initially require changing daily but can be extended and left in place for up to 7 days. The dressing will need changing when the amount of fluid absorbed is detrimental to the continued support of the dressing by the selected fixation method. The dressing should be changed when the weight of absorbed fluid becomes uncomfortable for the patient or reaches capacity.

EXAMPLE 2

Fluid Uptake by and Anti-Bacterial Properties of Honey/Super-Absorbent Compositions Tests were conducted to assess the water uptake of and anti-bacterial activity of honey impregnated OASIS SAF® materials, the results of which are provided in Table 1 below.

Methods

Antibacterial activity: A 12.6 mm OD cork borer was used to prepare circles of dressing to be placed on *Staphylococcus aureus* seed agar prepared in petri dishes and test tubes (13 mm diameter). Dressing circles were placed onto the surface of the agar and incubated overnight.

Water uptake: A 2 cm square piece of each dressing was placed onto a 7.5×7.5 cm square of curtain voile. The dressing and voile was placed onto a wet paper towel in a tray, covered with another tray to retain moisture and left at room temp. Voile and dressing was weighed at intervals until no more increase in weight was detected.

In each case, the dressing was a OASIS SAF® sheet impregnated with Manuka honey and four dressings were tested.

Results

As seen from Table 1, the dressings cleared zones of *Staphylococcus aureus* in both agar plates and test tubes, demonstrating their anti-bacterial activity. Further, all dressings were shown to be capable of water uptake.

EXAMPLE 3

Analysis of CMC Coated OASIS SAF® 2577 Impregnated with Honey

Tests were conducted on OASIS SAF® 2577 impregnated with honey and coated with a CMC.

100 cm$^2$ OASIS SAF® 2577 (dry weight 1.5 g) was impregnated with Manuka honey (impregnated weight 25 g) and coated with one of two CMCs (tests 2A and 2B in FIG. 2), before immersing in 100 ml water. Weights were recorded at 1 hour and 3 hours from immersion.

It was noted that coating with CMC led to the formation of a gel layer in the presence of water, which gel layer was discoloured by the honey indicating the presence of honey in the gel layer on the surface of the dressing. This is indicative of the release of honey from the dressing (FIG. 2). FIG. 2 clearly illustrates the absorption property and surface gelling.

The invention claimed is:

1. A composition comprising honey and a super-absorbent polymer fiber, which super-absorbent polymer fiber provides a lattice structure and is impregnated with the honey, wherein (a) the super-absorbent polymer fiber comprises a cross-linked polymer of acrylic acid and methacrylate; (b) the honey utilizes less than 50% of the super-absorbent polymer fiber's absorbent capacity; (c) the weight ratio of honey to super-absorbent polymer fiber is at least 2:1; and (d) the superabsorbent polymer fiber is able to absorb, in water, at least 10 times its dry weight whilst retaining structural integrity of the composition.

2. A composition according to claim 1 wherein the composition is in the form of a semi-solid pliable sheet.

3. A composition according to claim 2 wherein the sheet comprises at least one layer of a cellulose compressed material or polyester, interspersed with at least one layer of a super absorbent polymer fiber.

4. A composition according to claim 3, wherein the cellulose compressed material is tissue paper.

5. A composition according to claim 2, wherein the sheet comprises a mixture of a super-absorbent polymer fiber and a cellulose fiber in a non-layered structure.

6. A composition according to claim 2, wherein thickness of the sheet is between 0.25 mm and 10 mm.

TABLE 1

| Dressing Ref | Antibacterial Activity | | Water uptake | | | | | | |
|---|---|---|---|---|---|---|---|---|---|
| | Plates Diameter of zone | Tubes Depth of zone | Weight at Time (To) Zero | 3 hrs | 5.5 hrs | 22.5 hrs | 28.5 hrs | Mx wt. To wt. | % uptake |
| 2294 | 33.65 | 5.75 | 2.182 | 3.583 | 3.563 | 3.485 | 3.488 | 1.306 | 60 |
| 2273 | 37 | 6.48 | 1.498 | 2.695 | 2.709 | 2.628 | 2.55 | 1.211 | 81 |
| 2577 | 32.12 | 5.98 | 1.424 | 2.941 | 3.15 | 3.208 | 3.176 | 1.784 | 125 |
| 2342 | 28.25 | 6.33 | 1.479 | 3.002 | 2.985 | 2.993 | 2.959 | 1.514 | 102 |

7. A composition according to claim 2, wherein thickness of the sheet is less than 1 mm.

8. A composition according to claim 1, wherein the honey utilizes between 5% and 50% of the super-absorbent polymer fiber's capacity.

9. A composition according to claim 1, wherein the honey utilizes less than 10% of the super-absorbent polymer fiber's absorbent capacity.

10. A composition according to claim 1, wherein antimicrobial activity of the honey is equivalent to a solution with a phenol content of at least 10%.

11. A composition according to claim 1, wherein the honey is Manuka honey.

12. A composition according to claim 1, wherein the composition is coated with a gelling agent.

13. A composition according to claim 12, wherein the gelling agent is in the form of a powder or granule or sheet.

14. A composition according to claim 12, wherein the gelling agent is any one or more of a super-absorbent polymer, alginate or carboxy-methyl-cellulose.

15. A composition according to claim 14, wherein the gelling agent is carboxy-methyl-cellulose.

16. A dressing comprising a composition according to claim 1.

17. A dressing according to claim 16, wherein the composition is encased within a fluid permeable material.

18. A dressing according to claim 17, wherein the fluid permeable material is selected from the group consisting of a non-woven, woven, knitted or other textile material of synthetic or natural origin, and a polymer film.

19. A dressing according to claim 17, wherein the fluid permeable material is a polymer based non-woven material.

20. A dressing according to claim 19, wherein the polymer based non-woven material is selected from the group consisting of polyester, polyurethane, polypropylene and polyethylene.

21. A composition according to claim 1 or a dressing according claim 16, which is sterile.

22. A method of treating a lesion, comprising applying a composition according to claim 1 or a dressing according to claim 16 to the lesion.

23. A method of manufacturing a composition according to claim 1, comprising:
   (a) providing at least one type of honey;
   (b) providing at least one super-absorbent polymer fiber; and
   (c) combining the honey and super-absorbent polymer fiber.

24. A method of manufacturing the dressing according to claim 17, comprising:
   (a) providing a composition as defined in claim 1; and
   (b) encasing the composition within a fluid permeable material.

* * * * *